(12) United States Patent
Castaldi et al.

(10) Patent No.: US 6,515,181 B2
(45) Date of Patent: Feb. 4, 2003

(54) PROCESS FOR THE PREPARATION OF TERBINAFINE

(75) Inventors: Graziano Castaldi, Briona (IT); Giuseppe Barreca, Montevecchia (IT); Renzo Rossi, Pisa (IT)

(73) Assignee: Dipharma S.p.A., Basiliano (IT)

( * ) Notice: Subject to any disclaimer, the term of this patent is extended or adjusted under 35 U.S.C. 154(b) by 0 days.

(21) Appl. No.: 10/085,699

(22) Filed: Feb. 28, 2002

(65) Prior Publication Data

US 2002/0123651 A1 Sep. 5, 2002

(30) Foreign Application Priority Data

Mar. 2, 2001 (IT) .......................... MI01A0430

(51) Int. Cl.[7] ............................................ C07C 211/00
(52) U.S. Cl. ....................................................... 564/387
(58) Field of Search ........................................ 564/387

(56) References Cited

U.S. PATENT DOCUMENTS 4,755,538 A * 7/1988 Hawrylko
5,817,875 A * 10/1998 Karimian et al.

OTHER PUBLICATIONS

Alami et al, Tetrahedron Letters (1996), 37(1), pp. 57–58.*
Alami et al, Journal of Organometallic Chemistry, (2001), 624(1–2), pp. 114–123.*

* cited by examiner

*Primary Examiner*—Samuel Barts
(74) *Attorney, Agent, or Firm*—Bucknam and Archer

(57) ABSTRACT

A process for the preparation of terbinafine which comprises the reaction of tert-butylacetylene with a compound of formula (II)

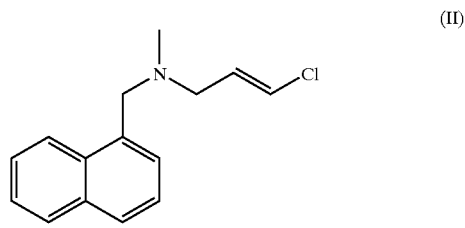

(II)

characterized in that the reaction is carried out in the presence of copper (I) salts and of a base, in the absence of palladium.

6 Claims, No Drawings

PROCESS FOR THE PREPARATION OF TERBINAFINE

The present invention relates to a process for the preparation of terbinafine or (E)-N-(6,6-dimethyl-2-hepten-4-ynyl)-N-methyl-1-napthalene methanamine, a known medicament with antifungal activity for the topical use, belonging to the propenylamine class, whose formula is reported below:

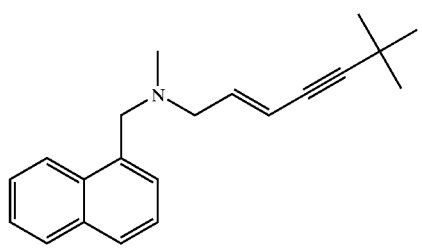

(I)

Prior Art

Terbinafine has been disclosed in U.S. Pat. No. 4,755,538, which reports a number of methods for the preparation thereof. In particular, the described processes involve:
a) alkylation of N-methyl-1-napthalenemethylamine with trans-6,6-dimethylhept-2-en-4-ynyl-1-bromide;
b) catalytic hydrogenation of N-methyl-N-(1-napthalenemethyl)-6,6-dimethylhept-2,4-dienyl-1-amine;
c) reductive amination 1-naphthylmethylamine with trans-6,6-dimethylhept-2-en-4-yn-1-al in the presence of formaldehyde and sodium borohydride.

Said processes are however not convenient in that the undesired stereoisomer (Z) is also formed, which has then to be removed with chromatographic procedures.

U.S. Pat. No. 5,817,875 discloses other processes, which comprise the reaction of N-methyl-1-napthalenemethylamine with epichlorohydrin or with bromoacetaldehyde dialkylacetal, followed by the introduction of the alkyne side chain by reaction of the epoxy group with a lithium tert-butylacetylene and subsequent dehydration, or by reaction of the acetal carbonyl with a suitable ilide according to Wittig. In this case also, the Z isomer is still present in addition to the desired isomer.

Stereospecific synthesis for the preparation of terbinafine using organometal reagents have also been described.

In a paper by A. Stutz et al., (Int. Conf. Organomet. Chem. 1274; 1985 Abs. 329), 6,6-dimethylhept-1-en-4-ynyl-3-hydroxy is acetylated and condensed with N-methyl-1-napthalenemethylamine in the presence of palladium(0) tetrakis(triphenylphosphine) and triethylamine to yield terbinafine and its (Z)-isomer. Some degree of selectivity towards one of the isomers can be obtained by changing the experimental conditions and using a catalyst of palladium linked to a polymer (B. M. Trost et al., J. Am. Chem. Soc., 100, 7779; 1978).

A further stereoselective synthesis of terbinafine has been described by D. E. Rudisile, L. A. Castonguay and J. K. Stille in Tetrahedron Lett., 29. 13. 1509–15; 1988.

This work is based on the fact that the coupling reactions between vinyl halides and alkynyl-stannanes catalyzed by palladium give high yields and maintain the stereochemistry of the double bond.

A synthesis of terbinafine and, more generally, of amino-enin derivatives has been described by M. Alani et al., in Tetrahedron Lett., 37, 1, 57–8; 1996, and comprises the reaction of aminovinyl chlorides 1-alkynes in the presence of complexes of palladium in piperidine.

The Authors disclose that amination of (E)-1,3-dichloropropene with N-methyl-1-napthalenemethylamine in acetonitrile in the presence of potassium carbonate and a catalytic amount of potassium iodide (10%) selectively yields the corresponding (E)-vinyl chloride. The resulting product is reacted with tert-butylacetylene in the presence of piperidine and a catalytic amount of palladium dichlorodibenzonitrile and copper(I)iodide to stereospecifically obtain terbinafine (I) in almost quantitative yields. Substantially similar processes are also disclosed in EP 421302, EP 645369, U.S. Pat. Nos. 5,231,183, 5,296,612, WO 01/77064 and WO 02/02503.

DISCLOSURE OF THE INVENTION

It has now been found that terbinafine can advantageously be obtained by reaction of tert-butylacetylene with a compound of formula (II)

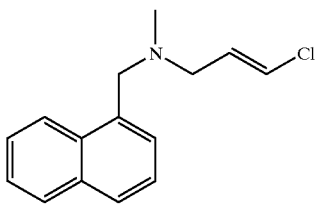

(II)

in the presence of copper (I) salts and of a base.

The process according to the invention is an improvement to the method described by Alani M et al, cited above, in which the same reaction is carried out suing two metal catalysts, one based on palladium and the other based on copper. The possibility to use only the copper salt indeed makes the work up and purification steps easier while preventing the final product from being contaminated by palladium.

Furthermore, the process of the invention is advantageous in terms of yields and selectivity.

Suitable copper (I) salts for use according to the invention are halides, preferably iodide.

Amines such as pyridine, piperidine, piperazine, morpholine, diisopropylamine, triethylamine, n-octylamine, n-butylamine, picoline and the like may preferably be used as bases, n-butylamine being particularly preferred.

The reaction is carried out optionally in the presence of a solvent at a temperature ranging from 20° C. to 100° C., preferably 60°–90° C., in the presence of a catalytic amount of copper (I) salt ranging from 1% to 30% molar, preferably 10–20% molar.

The following examples illustrate the invention in greater detail.

EXAMPLE 1

Preparation of Crude Terbinafine

A solution of vinyl chloride (II) (1.9 g; 7.73 mmoles) in n-butylamine (2.8 g; 38.6 mmoles), is added with tert-butylacetylene (0.8 g; 9.74 mmoles) and copper(I)iodide (0.30 g; 1.55 mmoles). The mixture is heated under inert atmosphere at a temperature of 80° C., keeping these conditions for 22 hours.

The suspension is cooled at room temperature, then diluted with toluene (20 mL) and water (10 mL). The phases are separated and the upper toluene phase is concentrated to a residue under vacuum.

2.3 g of a thick oil consisting of crude terbinafine is obtained.

¹H NMR (CDCl₃, δ in ppm): 1.25 (s, 9H), 2.22 (s, 3H), 3.13 (dd, 2H), 3.90 (s, 2H), 5.67 (m, 1H), 6.15 (m, 1H), 7.36–8.31 (aromatics, 7H).

GC-MS (m/and): 291 (M*⁺), 276, 234, 196, 141.

EXAMPLE 2

Preparation of Crude Terbinafine

A solution of vinyl chloride (II) (1.9 g; 7.73 mmoles) in piperidine (3.3 g; 38.6 mmoles), is added with tert-butylacetylene (0.8 g; 9.74 mmoles) and copper(I)iodide (0.30 g; 1.55 mmoles). The mixture is heated under inert atmosphere at a temperature of 80° C., keeping these conditions for 22 hours.

The suspension is cooled at room temperature, then diluted with toluene (20 mL) and water (10 mL). the phases are separated and the upper toluene phase is concentrated to a residue under vacuum.

2.4 g of a thick oil consisting of crude terbinafine is obtained.

EXAMPLE 3

Preparation of Crude Terbinafine

A solution of vinyl chloride (II) (1.9 g; 7.73 mmoles) in dimethylformamide (3.8 mL) is added with n-butylamine (1.12 g; 15.5 mmoles), tert-butylacetylene (0.8 g; 9.74 mmoles) and copper(I)iodide (0.30 g; 1.55 mmoles). The mixture is heated under inert atmosphere at a temperature of 100° C., keeping these conditions for 24 hours.

The suspension is cooled at room temperature, then diluted with toluene (20 mL) and water (10 mL). The phases are separated and the upper toluene phase is concentrated to a residue under vacuum.

2.6 g of a thick oil consisting of crude terbinafine is obtained.

EXAMPLE 4

Preparation of Crude Terbinafine

A solution of vinyl chloride (II) (1.9 g; 7.73 mmoles) in n-butylamine (2.8 g; 38.6 mmoles), is added with tert-butylacetylene (0.8 g; 9.74 mmoles) and copper(I)iodide (0.07 g; 0.38 mmoles). The mixture is heated under inert atmosphere at a temperature of 80° C., keeping these conditions for 40 hours.

The suspension is cooled at room temperature, then diluted with toluene (20 mL) and water (10 mL). The phases are separated and the upper toluene phase is concentrated to a residue under vacuum.

1.5 g of a thick oil consisting of crude terbinafine is obtained.

EXAMPLE 5

Preparation of Crude Terbinafine

A solution of vinyl chloride (II) (1.9 g; 7.73 mmoles) in n-butylamine (2.8 g; 38.6 mmoles), is added with tert-butylacetylene (0.8 g; 9.74 mmoles) and copper(I)bromide (0.33 g; 2.28 mmoles). The mixture is heated under inert atmosphere at a temperature of 80° C., keeping these conditions for 22 hours.

The suspension is cooled at room temperature, then diluted with toluene (20 mL) and water (10 mL). The phases are separated and the upper toluene phase is concentrated to a residue under vacuum.

1.8 g of a thick oil consisting of crude terbinafine is obtained.

EXAMPLE 6

Preparation of Terbinafine Hydrochloride

A solution of crude terbinafine (example 1, ~7.7 mmoles) in acetone (16 mL) is added with a 37% w/w hydrochloric acid solution (0.76 g, 7.7 mmoles). Crystallization is obtained by seeding with pure terbinafine hydrochloride while cooling −10° C.

After 1 hour the mixture is filtered and the solid is washed with acetone, then dried to obtain 2.0 g of pure terbinafine hydrochloride as a white solid (80% yield starting from vinyl chloride II).

¹H NMR (DMSO d₆, δ in ppm): 1.18 (s, 9H), 2.52 (d, 3H), 3.90 (m, 2H), 4.78 (m, 2H), 6.00 (d, 1H), 6.24 (m, 1H), 7.43–8.43 (aromatics, 7H), 11.4 (s, 1H).

HPLC purity: 99.93%

Melting point: 205°–206° C.

What is claimed is:

1. A process for the preparation of terbinafine, which comprises reacting tert-butylacetylene with a compound of formula (II)

characterized in that the reaction is carried out in the presence of copper (I) salts and of a base, in the absence of palladium.

2. A process as claimed in claim 1, wherein the copper (I) salts are the halides.

3. A process as claimed in claim 2, wherein the copper (I) salt is the iodide.

4. A process as claimed in claim 1, wherein the bases are amines.

5. A process as claimed in claim 4, wherein the bases are selected from pyridine, piperidine, piperazine, morpholine, diisopropylamine, triethylamine, n-octylamine, n-butylamine, picoline.

6. A process as claimed in claim 5, wherein the base is n-butylamine.

* * * * *